US006468787B1

(12) United States Patent
Affleck et al.

(10) Patent No.: US 6,468,787 B1
(45) Date of Patent: Oct. 22, 2002

(54) METHOD AND APPARATUS FOR CONTROLLED PHOTOELUTION

(75) Inventors: Rhett L. Affleck, Lawrenceville, NJ (US); Doug Hobbs, Lansdale, PA (US); Ilya Feygin, Mountainside; Gregory L. Kirk, Skillman, both of NJ (US); James A. Connelly, Falls Township, PA (US); Ning Zhao, West Windsor; James P. Mueller, Cranbury, both of NJ (US); Peter Kieselbach, Upper Black Eddy, PA (US)

(73) Assignee: Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 09/294,169

(22) Filed: Apr. 19, 1999

Related U.S. Application Data

(62) Division of application No. 08/914,861, filed on Aug. 19, 1997.
(51) Int. Cl.[7] ............................ C12M 1/00; B32B 27/12
(52) U.S. Cl. .............................. 435/292.1; 435/294.1; 435/DIG. 44; 422/135; 422/186.3
(58) Field of Search ................................. 47/17, 39, 58, 47/60, 65, 79, 46, 45, 6, 1.55, 82; 211/DIG. 6; 422/63.1, 129, 135, 186.3; 435/283.1, 289.1, 292.1, 294.1, 299.1, 302.1, DIG. 44

(56) References Cited

U.S. PATENT DOCUMENTS

| 4,817,332 | A | * | 4/1989 | Ikeda et al. ..................... 47/17 |
| 5,143,854 | A | * | 9/1992 | Pirrung et al. .............. 436/518 |
| 5,584,141 | A | * | 12/1996 | Johnson ......................... 47/65 |

OTHER PUBLICATIONS

Faber, Landis on Mechanics of Claim Drafting, 3rd Edition, Practising Law Institute, p. 131 and 533, 1990.*

Merriam–Webster's Collegiate Dictionary, Tenth Edition, pp. 55 and 65, 1999.*

* cited by examiner

*Primary Examiner*—Padmashri Ponnaluri
(74) *Attorney, Agent, or Firm*—DeMont & Breyer, LLC

(57) ABSTRACT

A method for photoeluting photocleavable linker-attached chemical compounds, and an apparatus suitable for implementing the method, are disclosed. According to the method, photocleavable linker-attached library compounds are photoeluted from solid support media under conditions of controlled light exposure and controlled temperature. An apparatus suitable for carrying out the present photoelution method includes means for substantially evenly illuminating the photocleavable linker, means for controlling illumination time and intensity, and means for controlling sample temperature.

20 Claims, 5 Drawing Sheets

METHOD AND APPARATUS FOR CONTROLLED PHOTOELUTION

This is a divisional of application Ser. No. 08/914,861, filed Aug. 19, 1997.

FIELD OF THE INVENTION

The present invention relates to the field of solid-phase chemistry. More particularly, the present invention relates to a method and apparatus for eluting photocleavable-linker attached chemical library compounds.

BACKGROUND OF THE INVENTION

Combinatorial chemistry libraries or single chemistries can be produced by a method known as solid-phase synthesis. That process involves linking a first chemical "base structure" molecule to solid support media and subsequently adding, seriatim, chemical building blocks, or, alternatively, effecting chemical structural changes to the base structure, e.g., ring opening or closing. The base structure molecule participates in one or more reaction steps with the added chemical building blocks. Chemical compounds, referred to as library compounds, descended from the base structure molecule, are thereby generated. Extremely large, diverse chemistry libraries can be synthesized in this manner.

Each library compound, and its base structure molecule precursor, is typically attached to the solid support media, typically inorganic or polymer beads, via a cleavable linker that covalently links the compound to the support media. The synthesized library compound remains linked to the support media until such time as it is deliberately removed therefrom. A synthesized library compound can be separated from the support media by cleaving the linker. One class of linkers, referred to as photocleavable linkers, are cleaved by exposure to light, such as long-wave ultraviolet light (UV). The process by which a synthesized compound is cleaved from the photocleavable linker and removed from the environment of the solid support media is termed photoelution.

Currently, chemists use mercury spot lamps for photoelution. While such a spot lamp generates sufficient light output, it provides uniform illumination across a relatively small circular region or spot on the order of 5 centimeters or less in diameter. As such, they are suitable for illuminating only one sample at a time. As conventionally practiced, a spot lamp and sample are placed inside a hood. Due to the amount of bench-top area required, only one or two lamps are typically placed within a given hood, limiting the amount of samples that can be photoeluted. Moreover, the small size of the uniformly illuminated region disadvantageously increases the likelihood of sample-to-sample variation in the amount of received radiation.

As such, it would be desirable to have a method and apparatus for simultaneously photoeluting a multiplicity of samples and for providing a substantially uniform dosage of radiation thereto.

SUMMARY OF THE INVENTION

A method for photoelution, and an apparatus suitable for implementing the method, are disclosed. According to the present method, photocleavable linker-attached library compounds are photoeluted from solid support media by (i) exposing the solid support media for a portion of the photoelution time to light having a spectral energy distribution appropriate for cleaving the photocleavable linker from the solid support, and (ii) eluting the library compound from the solid support with a solvent under controlled temperature with or without UV exposure.

An apparatus suitable for carrying out the present photoelution method includes means for substantially evenly illuminating the sample, means for controlling illumination time and intensity, and means for controlling sample environment including temperature and, optionally, atmosphere. In some embodiments, means for substantially evenly illuminating the sample includes means for stirring or agitating the sample.

BRIEF DESCRIPTION OF THE DRAWINGS

Further features of the invention will become more apparent from the following detailed description of specific embodiments thereof when read in conjunction with the accompanying drawings, in which.

DETAILED DESCRIPTION

The present invention is directed to a method and apparatus for photoeluting linker-attached chemical compounds from solid support media. As used in this specification, the term "photoeluting" refers to a method by which (i) photocleavable linker is cleaved, thereby releasing the chemical compound from the solid support media, and (ii) the chemical compound is eluted out of the solid support media and into a solvent. The compounds, either attached, via linker, to the solid support media before photoelution, or in a linker-free or released state after photoelution, will be referred to herein as library compounds. It should be understood that such compounds may or may not be part of a chemical library.

Figure 1:
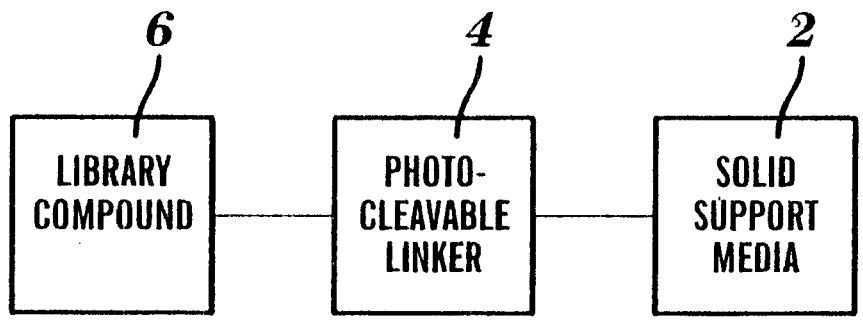
FIG. 1 represents a library compound linked to a solid support media via a linker.

FIG. 1 shows a simplified conceptual illustration of a library compound 6 linked to solid support medium 2 via a photocleavable linker 4. As used herein, the term "photocleavable linker" or "linker" means any component capable of being photolytically cleaved to release the library compound from the solid support media. See, e.g., Greene and Wuts, "Protective Groups in Organic Synthesis," 2d. ed., Wiley, 1991, incorporated by reference herein. In a preferred embodiment, the linker is o-nitrobenzyl. Solvents suitable for eluting released library compounds include, without limitation, acetonitrile, alcohols, such as ethanol, isopropanol, methanol, and the like, methylene chloride, water, and various stoichiometric and ratiometric mixtures thereof.

Solid support media 2 suitable for use in conjunction with the present invention include, without limitation, beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and soluble supports such as polyethylene glycol or low molecular weight non-cross-linked polystyrene. In a preferred embodiment, 200 micron PEG-grafted polystyrene beads (sold under the trademark "TENTAGEL™," by Rapp Polymere of Tubingen, Germany) are used as the solid support media. In other embodiments, beads having a diameter within the range of about 0.01 to 10 millimeters (mm) may suitably be used.

Notwithstanding the designation as "solid," the solid support media 2 are characteristically porous so that substantially more than simply the external surface is accessed by library compounds 6. As such, it should be understood that while FIG. 1 shows linker 4 and library compound 6 apparently attached to an external surface 8 of the solid support media 2, a substantial amount of linker 4 and library compounds 6 are attached to inner surfaces, i.e., the surfaces of pores, within the solid support media 2.

In a method according to the present invention, photoelution reaction conditions are controlled to an extent not hitherto practiced in the art. More specifically, as illustrated by the flow diagram in FIG. 2, photoelution is carried out under conditions of controlled duration and intensity of light exposure and controlled temperature. Exemplary apparatuses for implementing the present method are described later in this specification.

Figure 3:
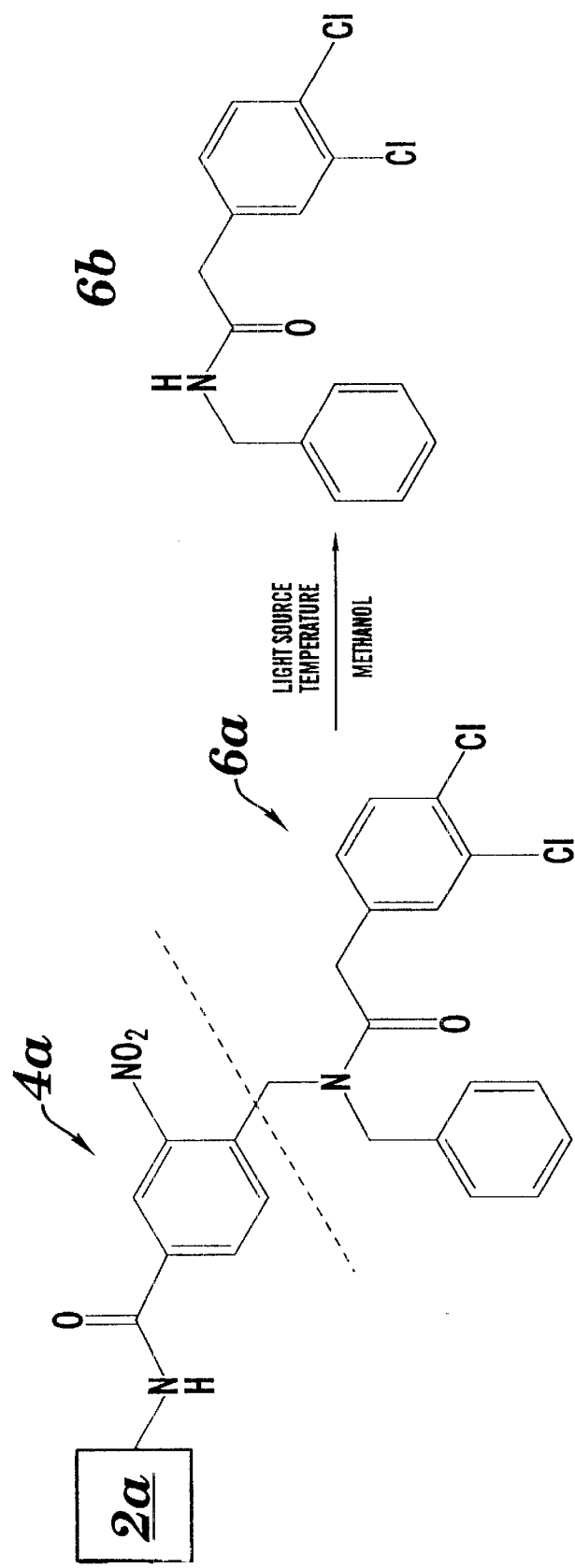
FIG. 3 shows the photocleavage reaction for o-nitrobenzyl linker.

As indicated in operation block 201, photocleavable linker is evenly irradiated for a predetermined time period by light having a spectral energy distribution appropriate for cleaving the linker from the library compound. The photocleavage reaction for o-nitrobenzyl linker is shown in FIG. 3. As shown in that Figure, o-nitrobenzyl linker 4a is attached to a library compound 6a and solid support media 2a. The reaction liberates the library compound 6a as a secondary amide 6b. Other leaving groups may result when different photocleavable chemistries are used.

Linker photolytic cleavage is dependent on the wavelength of the irradiating light, its intensity and duration. Long-wave UV, i.e., UV-A, which has spectral energy in the range of about 320–400 nanometers (nm), is suitable for cleaving o-nitrobenzyl linker. It should be understood that the aforementioned range is a compromise between using shorter wavelengths that may damage the library compound and using longer wavelengths that are less effective at cleaving the linker. Light having other spectral energy distributions may be required for cleaving other photocleavable linkers. Such other energy distributions are known to, or can be readily determined by, those of ordinary skill in the art.

It will be appreciated that due to the relatively small size of the solid support media, i.e., the beads, a relatively large number of such beads may be retained within a vial or other vessel for carrying out photoelution. Irradiating light should be delivered substantially evenly to all such beads. This is best accomplished, in certain embodiments, using an agitating or stirring device. An exemplary stirring device is a standard stirring bar activated by a motor-driven magnet. Thus, in block 201, the operation of evenly irradiating the linker may further include a controlled mixing or agitating operation. It will be understood that if the solid support media are retained within a plate having relatively shallow sample-receiving regions or wells, such as a microtiter plate, a stirring device may not be required to achieve substantially uniform illumination.

Continued UV irradiation after linker photocleavage may degrade released library compounds. In particular, library compounds that have been released from the linker but that have not diffused out of the solid support media are particularly vulnerable to such degradation. As such, it is desirable to limit the extent of UV irradiation to no more than that required for cleaving a desired fraction of total linker bonds. With a suitably intense light source, the time required for UV irradiation is shorter than the total time required for released library compounds to be cleaved from the supports and to diffuse out of the solid support media. Thus, in operation block 201, the predetermined time period for illumination is suitably short for limiting degradation of released library compounds.

Figure 4:
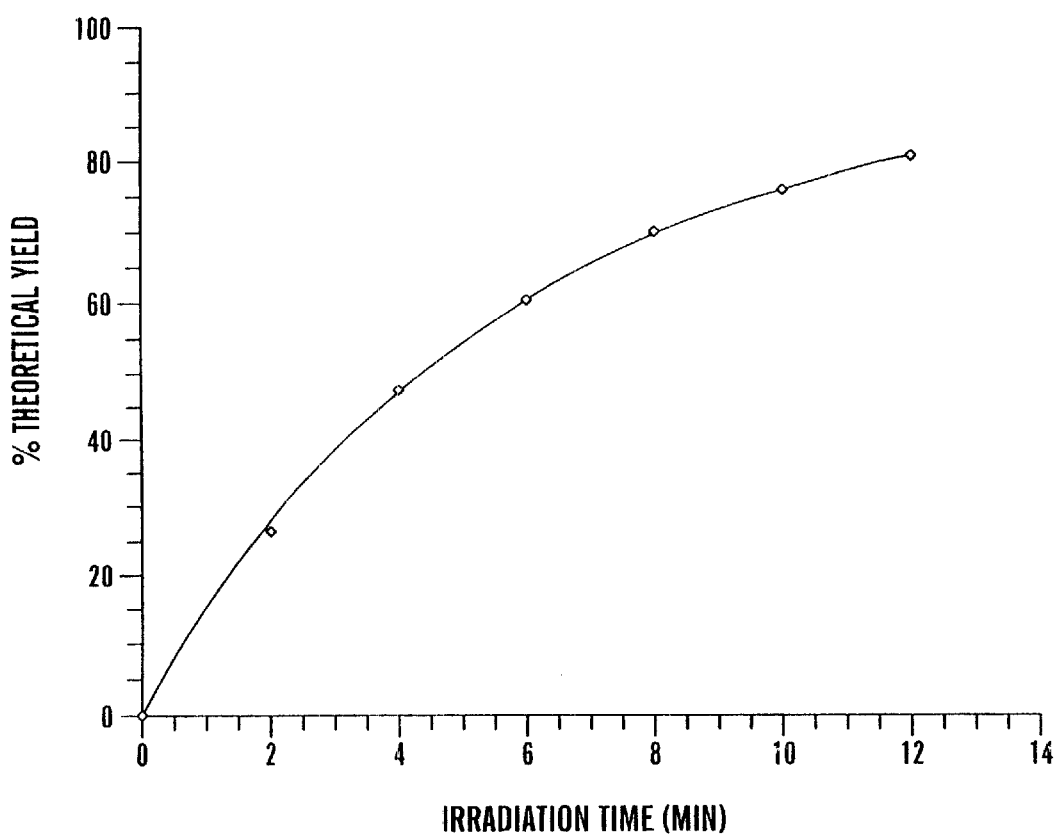
FIG. 4 shows a plot of percent theoretical yield of photocleaved linker as a function of time.

The fractional extent of linker cleavage, i.e., the proportion of linkers cleaved out of the total of linkers present, can be controlled by irradiation time. Moreover, reaction rate will be affected by the spectral energy distribution of the irradiating light, as well as its intensity. It has been experimentally determined that photocleaving reaction kinetics follow a first order decay below about 50 milliwatts per square centimeter (mW/cm$^2$) in the UV-A range mentioned above. FIG. 4 shows a plot of the percentage of theoretical yield of photocleaved linker (as determined by measurement of eluted compound) as a function of irradiation time for a given solvent, bulb type, light intensity and linker and library compound chemistry. The photocleaving rate expression can be readily determined from such data. The rate equation for other solvents, light sources, light intensities, linker and library compound chemistries can be determined with simple experimentation by those of ordinary skill in the art.

In one embodiment of the invention, illumination occurs in one or more timed doses separated by equilibration periods. Sufficient light intensity is provided so that a dose lasts for a time period within the range of about one minute to five hours. Light intensity, as measured at the solid support media, in the range of from about 0.2 to about 10 (mW/cm$^2$) at 365 nm with a 10 nm bandpass is suitable for attaining dosing periods within the prescribed range. It will be understood that the present method can be practiced using a lower than recommended light intensity. Such a practice lengthens the illumination period. Shorter illumination periods are presently preferred so as to minimize overall photoelution time.

After each illumination period, the system can be allowed to equilibrate wherein linker-released library compounds elute out of the solid support media and into the solvent. Such an equilibration period is typically within the range of about one to twelve hours for the 200 micron TENTAGEL™ as a function of temperature.

Figure 2:
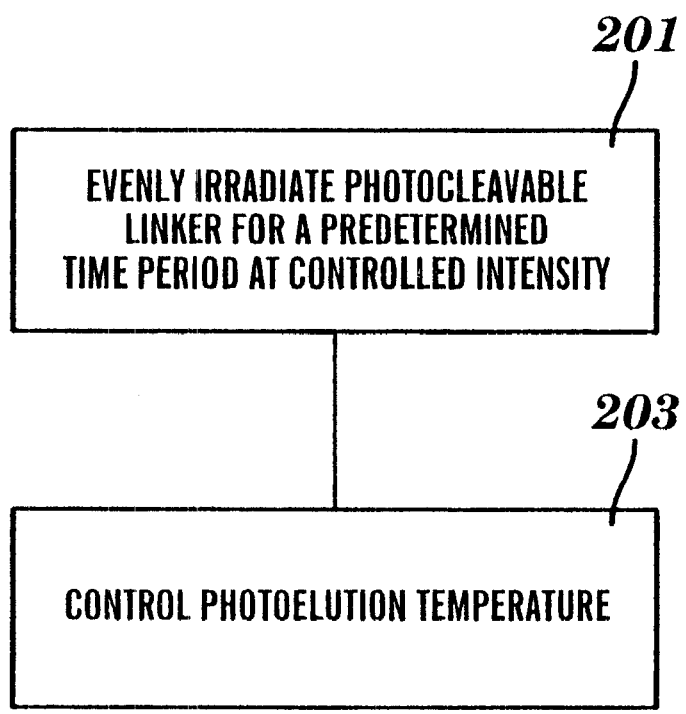
FIG. 2 shows a flow diagram of a method according to the present invention for photoeluting a photocleavable-linker-attached chemical library compound.

With continuing reference to FIG. 2, in a method according to the present invention, photoelution temperature is controlled as indicated in operation block 203. Preferred photoelution temperature is selected based on several parameters, including, without limitation, the particular solid support media used, the linker composition, and the solvent. Moreover, to the extent that at least some of the photoeluting library compounds are temperature-sensitive, as is often the case, the presence of such compounds may limit the maximum acceptable photoelution temperature. A photoelution temperature within the range of about 20° to 70° C. is suitable for photoeluting with o-nitrobenzyl linker, methanol as the solvent and, TENTAGEL™ beads as the solid support. The aforementioned range of photoelution temperatures is satisfactory if other linkers, solid support media and solvents are used, as well. To the extent that such a temperature range is unsuitable for use with certain other systems, those skilled in the art can readily determine such suitable conditions for such other systems in view of the present teachings.

According to the present method, it may be also desirable to expose samples to heat,but not light, e.g., UV, for some portion of time during photoelution.

Figure 5:
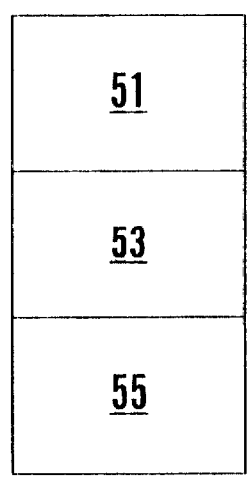
FIG. 5 shows a functional representation of an apparatus according to the present invention for photoeluting a photocleavable-linker-attached chemical library compound.

Prior art apparatuses or arrangements: for photoelution art, at best, poorly suited for implementing the present photoelution method. Accordingly, an apparatus suitable for providing the requisite control over photoelution operating conditions and, if desired, for providing heating in the absence of illumination, is described below. Such an apparatus, illustrated in FIG. 5, is functionally described as including means 51 for supplying uniform illumination and controlling illumination intensity, means 53 for controlling illumination time and means 55 for controlling sample temperature. Such an apparatus optionally includes means for controlling sample atmosphere.

Means 51 for supplying uniform illumination is typically a lamp having a spectral energy distribution suitable for cleaving the particular photocleavable linker being used in conjunction with the library compound. For example, as previously described, long-wave UV having some spectral energy in the range of about 320–400 nanometers (nm) is suitable for cleaving an o-nitrobenzyl linker. A bulb providing a light intensity at the sample in the range of about 0.2 to about 10 mW/cm$^2$ at 365 nm with a 10 nm bandpass has been found to be suitable for such purposes. Such intensity can be obtained using, for example, chemists' mercury spot lamps, available from UVP of California and BL9 phosphorescent bulbs, four feet long, 110 watts, available from Light Sources of Milford, Conne.

In some embodiments, means 51 for supplying uniform illumination further comprises means 57 for stirring, vibrating or agitating the sample to ensure that substantially all solid support media and attached linker and library compound receive about the same amount of illumination. One implementation of such means 57 is a magnetic stirring system. Other means of vibrating, shaking, or agitating are known to practitioners in the art and may suitably be used.

In a first basic embodiment, means 53 for controlling illumination time is simply an "on-off" switch for controlling power to the illumination source. In a somewhat more sophisticated second embodiment, a plurality of such switches are provided, one for each illumination source, i.e., bulb. In a third embodiment, means 53 comprises a "shield," optically opaque at the relevant wavelengths and physically adapted for placement between a sample and means 51 for supplying illumination. In a fourth embodiment, means 53 for controlling illumination time includes a suitably configured photoeluting apparatus to allow insertion or removal of individual vessels containing respective samples. In a fifth embodiment, means 53 includes a conveyor by which samples are passed through an illumination zone, the samples thereby receiving a desired amount of illumination.

In some embodiments, means 53 may be configured so that, if desired, only a selected portion of the samples are illuminated. Additionally, means 53 can be automatically controlled, such as, for example, by using a simple timer, computer or the like.

Means 55 for controlling sample temperature may suitably include, for example, a temperature-controlled fluid, preferably a liquid, in contact with the exterior of a sample-containing vessel. Alternatively, such means 55 may include a temperature-controlled surface in contact with the sample-containing vessel.

Other implementations of means 51 for supplying uniform illumination and controlling illumination intensity, means 53 for controlling illumination time, means 55 for controlling sample temperature and means 57 for stirring, vibrating or agitating known to those of ordinary skill in the art may be used in lieu of those described above.

Photoelution is typically practiced in one of two formats. Such formats are characterized or distinguished by the configuration of the vessel containing the solid support media. In particular, in a first format, the solid support media are retained within vials or other similarly-configured vessels. In a second format, the solid support media are retained in a flat vessel containing a multiplicity of shallow wells, such as a microtiter plate. A first and a second exemplary apparatus suitable for practicing the present method, using the respective first and second formats, are described below.

Figure 6:
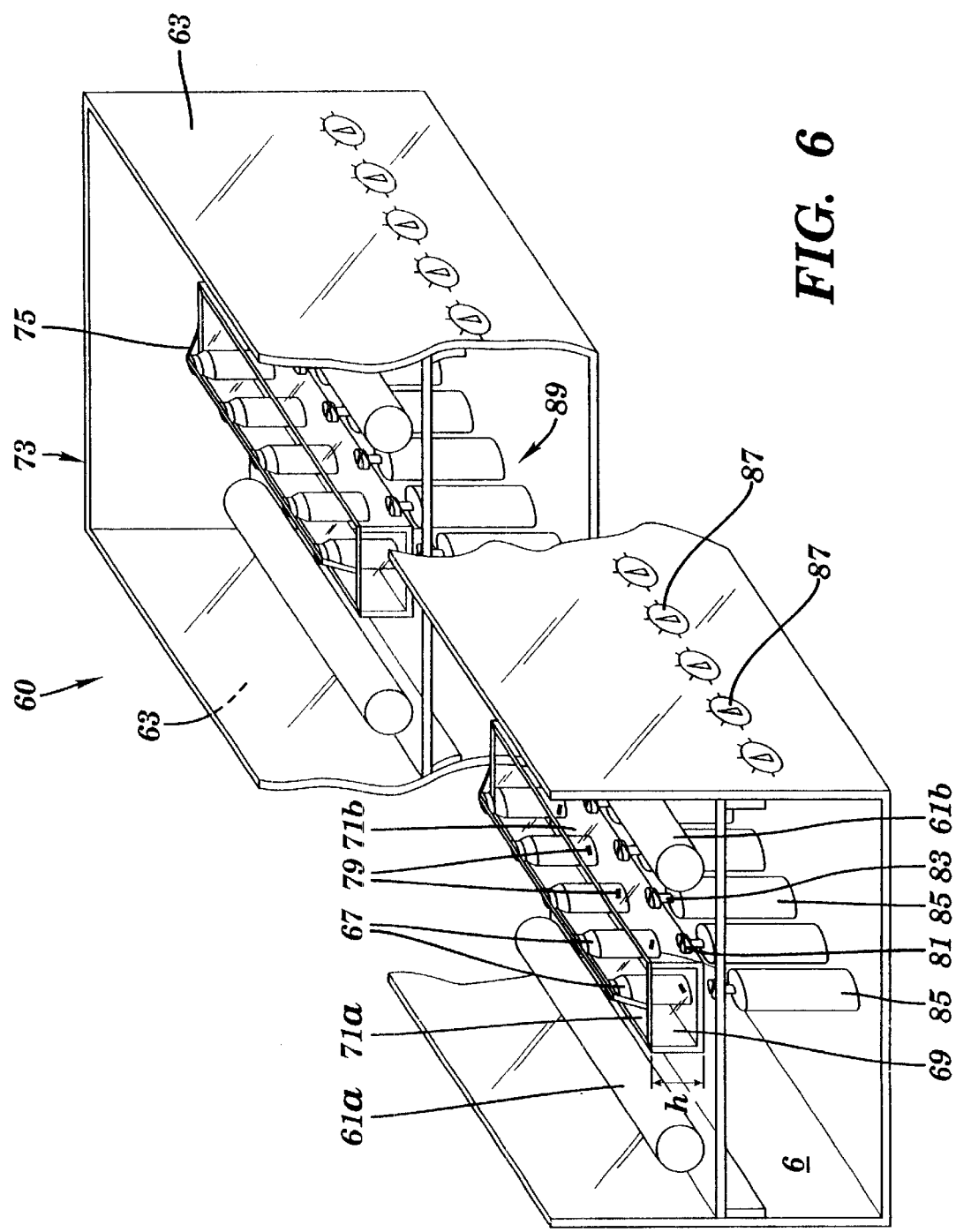
FIG. 6 shows an exemplary first embodiment of the apparatus of FIG. 5 wherein a vial is used for retaining the solid support media and linker-attached library compound.

FIG. 6 shows an exemplary first embodiment of the apparatus of FIG. 5 wherein a vial or similar cylindrical vessel is used for retaining solid support media with linker-attached library compound. For the exemplary apparatus 60 of FIG. 6, illumination is provided by two-bulbs 61a, 61b, which provide light having suitable spectral energy distribution and intensity as required for cleaving the selected photocleavable linker. The bulbs 61a, 61b are positioned, relative to a plurality of sample-containing vials 67, for providing uniform light exposure to such vials 67. In the embodiment shown in FIG. 6, the bulbs 61a, 61b flank the sample-containing vials 67. It should be appreciated that in other embodiments wherein the photoeluting apparatus is configured differently than in FIG. 6, fewer or additional bulbs, located in other positions, may suitably be used to provide uniform light exposure to the sample-containing vials 67.

In a presently preferred embodiment, two BL9 phosphorescent bulbs, four feet long (110 W) are used in the photoeluting apparatus 60. Such a longer-length bulb, in contrast to spot lights, advantageously provides substantially uniform illumination over most of its length. Such uniform illumination facilitates simultaneous photoelution of a plurality of samples, such as are contained in the plurality of sample-containing vials 67. A variety of different-sized vials may be so illuminated. Such an arrangement, allowing photoelution of samples contained in multiple vials in a relatively small space, i.e., about four feet of bench surface, represents a significant improvement over prior art photoelution apparatuses.

During at least a portion of the photoelution time, the sample-containing vials 67 are situated in a carrier exemplified by trough 69. The trough 69 is suitably configured to receive a flow of a temperature-controlled fluid, not shown, such as can be provided by an external fluid bath, such as a water bath, also not shown. Side walls 71a, 71b of trough 69 have a height h suitable for substantially submerging the sample-containing vials 67 within the received flowing temperature-controlled fluid. The flowing temperature-controlled fluid provides a stable, temperature-controlled environment for the vials 67 and the samples contained therein. In the exemplary photoelution apparatus 60, the external fluid bath and trough 69 embody the means 55 for controlling sample temperature.

To further control sample temperature, at least a partial thermal barrier, partition or the like between a sample-containing vial and the illumination source may be utilized. The barrier should be trans parent to the illuminating light at the appropriate wavelengths. In addition, an infrared filter may be used between the bulbs and the samples.

In the exemplary first embodiment shown in FIG. 6, sample-containing vials 67 may be disposed within the trough 69 during illumination. When so disposed, the side walls 71a, 71b of trough 69 are positioned between the vials 67 and respective bulbs 61a, 61b. Such side walls 71 are light (UV) transparent so that bulbs 61a, 61b provide a penetrating light exposure to the vials 67 through said side walls. Even illumination of the sample-containing vials 67 is hereby promoted. Suitable UV-transparent materials include, without limitation, glass, substantially UV-transparent polystyrene or acrylic, such as SUVT™ from Polycast Technology Corp. of Stanford, Conn.

The apparatus 60 further includes a retaining or hold down device 75, which may be configured, as in the exemplary apparatus 60, as a flexible string formed from a resilient and chemically stable material such as, for example, silicone tubing. Such a retaining device 75 secures sample-containing vials 67 against the bottom of the trough 69 to prevent floating of such vials 67 when flowing temperature-controlled fluid is present in the trough 69. Such a retaining device 75 is further physically adapted to avoid nonuniform illumination of the sample-containing vials 67, i.e., to avoid shadows.

As discussed in conjunction with FIG. 5, an apparatus for photoeluting according to the present invention includes means 53 for controlling illumination time. Such means may be implemented in numerous ways. For example, in the embodiment shown in FIG. 6, the trough 69 is accessible from a top 73 of the apparatus 60. Such access allows sample-containing vials 67 to be placed within, and removed from, the trough 69. Thus, at the end of a scheduled illumination period, one or more of the sample-containing vials 67 may be removed from the apparatus as required. Alternatively, opaque shields, not shown, can be placed between the bulbs and the samples. In one embodiment, the opaque shield is a UV-opaque cylinder open at least at one end. Such a cylinder is placed over a sample-containing vial 67, thereby preventing UV radiation from reaching the enclosed sample-containing vial 67 while maintaining sample temperature control.

The apparatus 60 further includes means for stirring or agitating the samples within the sample-containing vials 67 during photoelution. Agitating the sample during illumination promotes uniform illumination.

In the exemplary first embodiment shown in FIG. 6, the agitating means include one stirring bar 79 for each sample-containing vial 67. A plurality of motor-driven magnets 89, one for each sample-containing vial 67, are positioned beneath the trough 69. One motor-driven magnet 89 is located directly beneath each sample-containing vial 67.

Each motor-driven magnet 89 comprises a magnet 81 attached to a shaft 83 of a motor 85. Each motor 85 is controlled by an adjustable speed regulator 87. The motor-driven magnet 89 and stirring bar 79 are placed sufficiently close to one another so that the stirring bar 79 is actuatable by the magnetic field generated by the magnet 81. As the magnet 81 is rotated or otherwise moved by shaft 83 under control of the adjustable speed regulator 87, the stirring bar 79 moves in complimentary motion within the sample-containing vial 67. Such motion agitates the solid support media contained within vials 67.

Agitation of solid support media is monitored through optically transparent outer walls 63 and trough walls 71a, 71b. While transparent to light in the visible wavelength range, the outer walls 63 are substantially opaque to UV for safety considerations. Agitation is adjusted, via the adjustable speed regulator 87, to provide a sufficient amount of agitation to the solid support media. In the present context, "sufficient agitation" is the amount of agitation required for substantially uniformly illuminating all support media in a sample-containing vial. It has been found that if the stirring bar speed is adjusted to generate a vortex within a' sample-containing vial 67, the solid support media are sufficiently agitated for the present purposes. It will be appreciated that agitation speed for sufficiently agitating the solid support media is a function of the size of the stirring bar 79, the size of the sample-containing vial 67, the physical characteristics of the solid support media, and solvent viscosity and density, among other considerations.

It may be desirable to maintain the sample-containing vials 67 under an inert atmosphere such as, for example, nitrogen or argon. If so, the vials 67 can be sparged and then capped.

Figure 7:
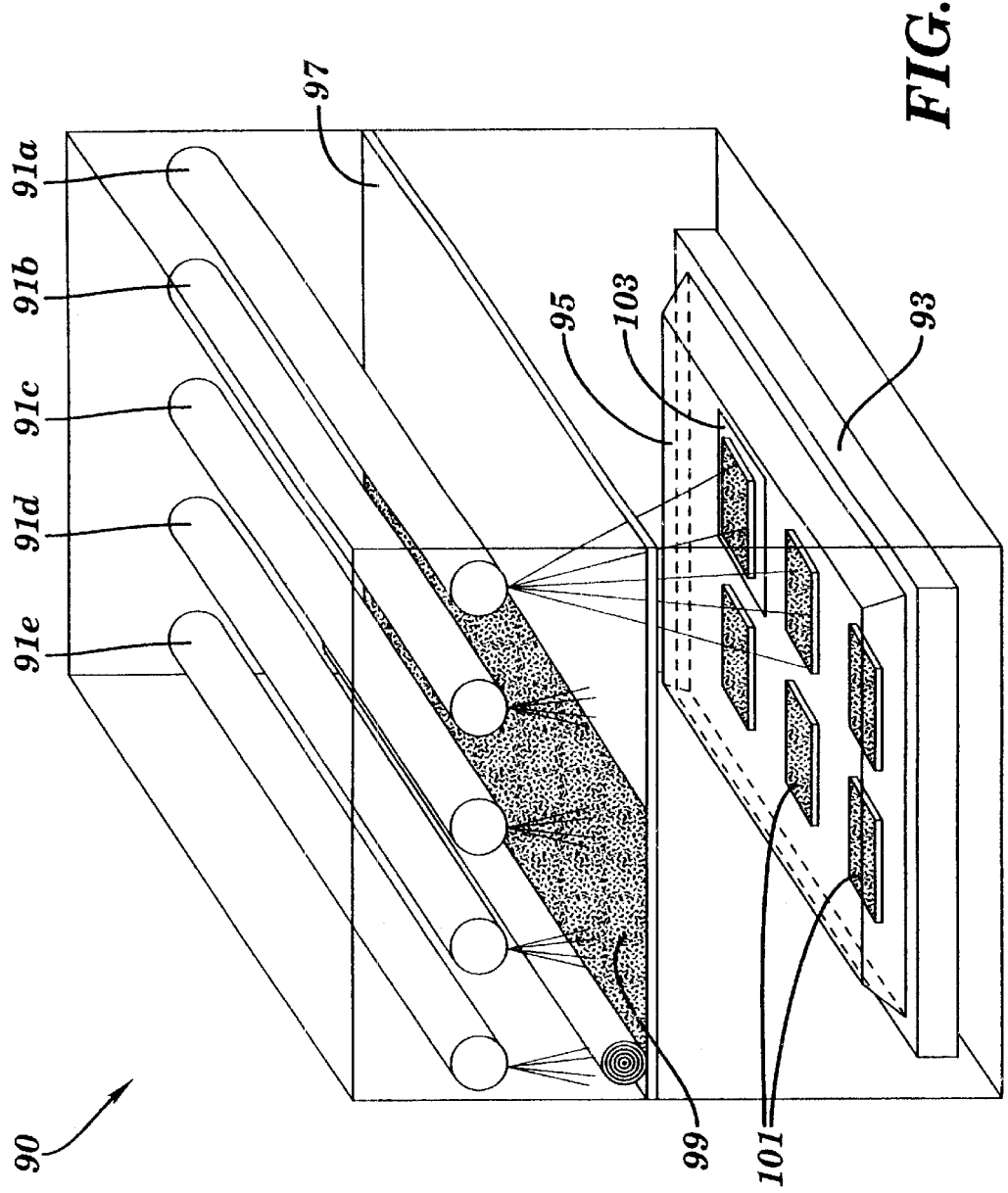
FIG. 7 shows an exemplary second embodiment of the apparatus of FIG. 5 wherein a microtiter plate retains the solid support media and linker-attached library compound.

FIG. 7 shows an exemplary second embodiment of the apparatus of FIG. 5 configured for photoeluting samples, comprising the solid support media with linker-attached library compounds, which are retained in microtiter plates 101. An example of plate 101 is a microtiter plate containing 96 wells.

Exemplary apparatus 90 of FIG. 7 includes a source of illumination having suitable spectral energy distribution and intensity as required for cleaving the selected photocleavable linker from the selected solid support media. In the exemplary embodiment shown in FIG. 7, the illumination source is five bulbs 91a–91e. The five bulbs 91a–91e are preferably the previously-described BL9 phosphorescent bulbs (110W). The bulbs 91a–91e are positioned, relative to a plurality of sample-containing plates 101, for providing uniform light exposure to the bottom of the wells contained in such plates 101, and to minimize shadows. Illumination intensity is controllable by simply changing the number of bulbs used for illuminating the sample-containing plates 101, via wattage selection or by regulating voltage which results in proportional changes in illumination intensity. Moreover, a neutral density filter 103 can be placed between the illumination source and individually-selected plates to moderate light intensity to the selected plates. Spectral or infrared filters may be used as well.

In the embodiment shown in FIG. 7, the five bulbs 91a–91e are located above the sample-containing plates 101. It should be appreciated that in other embodiments wherein the photoeluting apparatus is configured differently than in FIG. 7, fewer or additional bulbs located in other positions may suitably be used to provide uniform light exposure to the sample-containing plates 101. As previously described, long cylindrical bulbs, such as BL9 phosphorescent bulbs, advantageously provide more uniform illumination for photoeluting multiple samples than spot lights, and are used in preference thereto.

The apparatus for photoeluting illustrated in FIG. 7 also includes means for controlling illumination time. In the embodiment of FIG. 7, the sample-containing plates 101 are accessible from a side of the apparatus. Thus, plates 101 can be removed and inserted as required to control light exposure. Additionally, like the exemplary first embodiment, the exemplary second embodiment preferably incorporates a shield, opaque to the relevant wavelengths of light, which is positionable between the illumination source and a selected few or all of the sample-containing plates 101. In FIG. 7, the shield is implemented as a shutter 99 that is extendable, as required, across the surface of a thermal shield 97. The shutter is extended as far as necessary to prevent light from illuminating the selected few or all plates 101. In FIG. 7, the shutter 99 is shown extended about fifty percent of the distance across the barrier 97. Alternatively, a "Venetian blind" type of shield may be used.

In the embodiment of FIG. 7, temperature control is provided, primarily, by a temperature-controlled carrier, exemplified by surface or platen 93. Sample-containing plates 101 are placed on top of the platen. 93 and receive heat therefrom. The temperature-controlled platen 93 may include resistive elements, not shown, for generating heat on application of a current. Such current can be regulated by a servo that uses a temperature measurement of platen 93 or one of the wells of the sample-containing plates 101.

In one preferred embodiment, a cover 95, transparent to the illuminating light at the relevant wavelengths, is disposed on the platen 93 so as to substantially cover the sample-containing plates 101. The cover 95 provides additional temperature stability in the immediate vicinity of the sample-containing plates 101 by reducing convective heat transfer. In the exemplary photoelution apparatus 90, the temperature-controlled plate 93 and optional thermal barrier 97 embody the means 55 for controlling sample temperature.

The thermal barrier 97 segregates the apparatus 90 into first and second independently temperature-controllable regions. The first region includes the illumination source, e.g., the bulbs, and the second region includes the sample plates. The second region may optionally include a tap, not shown, for introducing and establishing an inert gas environment. Alternatively, the cover 95 can be fitted with a tap so that the inert gas may be introduced to the region underneath the cover 95.

Although a number of specific embodiments of this invention have been shown and described herein, it is to be understood that such embodiments are merely illustrative of the many possible specific arrangements that can be devised in application of the principles of this invention. Numerous and varied other arrangements can be devised in accordance with those principles by those of ordinary skill in the art without departing from the spirit and scope of the invention.

We claim:

1. An apparatus comprising:
    a carrier that receives a plurality of vials, wherein said vials contain samples, and wherein said samples comprise solid support media, and further wherein:
        said carrier has sidewalls depending from a bottom;
        said sidewalls are transparent to ultra violet radiation;
        said sidewalls and said bottom collectively define a region that receives and retains a flow of fluid that contacts said vials and controls a temperature of said samples within said vials; and
        said samples within said vials are isolated from said flow of fluid;
    a source of ultra violet light positioned to illuminate said samples in said vials; and
    an agitator that agitates said solid support media within said vials.
2. The apparatus of claim 1 further comprising a shield that is opaque to ultra violet light, wherein said shield is operative to prevent ultra violet light from illuminating at least one of said samples contained in one of said vials while allowing said flow of fluid to contact said one vial.
3. The apparatus of claim 2 wherein said shield is cylindrically shaped, open at one end thereof, and sized to fit over one of said vials.
4. The apparatus of claim 1 wherein a temperature of each of said samples is maintained within a range from 20° C. to 70° C. by said flow of temperature-controlled fluid.
5. The apparatus of claim 1 wherein said source of ultra violet light is two light bulbs that flank said carrier along a long axis thereof.
6. The apparatus of claim 5 wherein said two light bulbs are phosphorescent bulbs having an elongate, tubular shape.
7. The apparatus of claim 1 wherein said source of ultra violet light provides long wave ultra violet light having a spectral energy in a range of about 320 to 400 nanometers.
8. The apparatus of claim 1 wherein said agitator comprises:
    a plurality of stirring bars; and
    a plurality of motor-driven magnets, wherein:
        one of said stirring bars is disposed in each vial; and
        one of said motor-driven magnets is disposed beneath each vial.
9. The apparatus of claim 8 further comprising an adjustable speed regulator for controlling a speed of said motor-driven magnets.
10. The apparatus of claim 1 further comprising a hold down device operable to prevent said vials from floating when said carrier receives said flow of temperature-controlled fluid.
11. The apparatus of claim 1 further comprising outer walls for containing said carrier, said source of ultra violet light and said agitator, wherein said outer walls are transparent to visible light and opaque to ultra violet light.
12. An apparatus comprising:
    an enclosure;
    a temperature-controlled surface that is disposed within said enclosure, wherein said temperature-controlled surface receives a plurality of sample plates, wherein said sample plates contain samples, and wherein said samples comprise solid support media, and further wherein, when said temperature-controlled surface receives said sample plates, said sample plates are disposed on said temperature-controlled surface in heat-exchanging contact therewith so as to control a temperature of said samples within said sample plates;
    a source of ultra violet light that is disposed within said enclosure, wherein said source of ultra violet light is positioned to illuminate said samples; and
    a shield that is disposed within said enclosure, wherein said shield is opaque to ultra violet light and wherein said shield is controllable to selectively prevent some or all of said samples from being illuminated by said source of ultra violet light.
13. The apparatus of claim 12 comprising a cover that covers said plates thereby enclosing them between said temperature-controlled surface and said cover.
14. The apparatus of claim 12 further comprising a neutral density filter that is positionable between said source of ultra violet light and at least one of said plates to moderate an intensity of illumination to said one plate.
15. The apparatus of claim 12 further comprising a thermal barrier disposed between said source of ultra violet light and said temperature-controlled surface, said thermal barrier segregating said enclosure into first and second independently temperature-controllable regions, said first region including said source of ultra violet light, said second region including said temperature-controlled surface.

16. The apparatus of claim 12 wherein said shield comprises a shutter that is movable between:
   a first position, in which said shutter does not interfere with the illumination of any of said plates; and
   a second position, in which said shutter interferes with the illumination of all of said plates.

17. The apparatus of claim 12 wherein a temperature of each of said samples is maintained within a range from 20° C. to 70° C. by said temperature-controlled surface.

18. The apparatus of claim 12 wherein said source of ultra violet light is a plurality of light bulbs that are disposed above said temperature-controlled surface.

19. The apparatus of claim 18 wherein said plurality of light bulbs are phosphorescent bulbs having an elongate, tubular shape.

20. The apparatus of claim 12 wherein said source of ultra violet light provides long wave ultra violet light having a spectral energy in a range of about 320 to 400 nanometers.

* * * * *